United States Patent [19]

Young

[11] 3,963,422

[45] June 15, 1976

[54] COUNTER FLOWING POSITIVE ION-NEGATIVE ION NEUTRALIZATION CHROMATOGRAPH

[76] Inventor: Robert A. Young, R.R. No. 2, Loretto, Ontario, Canada

[22] Filed: July 12, 1974

[21] Appl. No.: 488,187

[52] U.S. Cl. ............................. 23/254 E; 250/493; 250/494; 356/74; 356/85; 317/3; 317/262 R
[51] Int. Cl.² .................... G01J 1/42; G01N 23/00; G01N 31/08
[58] Field of Search ...................... 23/254 E, 232 E; 250/493, 494; 315/111, 324; 356/85, 74; 317/3, 262 R

[56] References Cited
UNITED STATES PATENTS

| | | | |
|---|---|---|---|
| 3,233,136 | 2/1966 | Okagaki et al. | 356/74 UX |
| 3,354,315 | 11/1967 | Preston et al. | 356/85 |
| 3,489,942 | 1/1970 | Walsh et al. | 356/74 X |
| 3,514,604 | 5/1970 | Grojean | 356/85 X |
| 3,540,851 | 11/1970 | Vree et al. | 23/232 E |
| 3,591,289 | 7/1971 | Donega | 356/85 |
| 3,821,555 | 6/1974 | Mattsson | 250/494 X |

*Primary Examiner*—Robert M. Reese

[57] ABSTRACT

A counter flowing positive ion-negative ion neutralization chromatograph for analyzing gas samples containing helium and a species which forms negative ions. Two helium resonance lamps are mounted in a chamber with their windows in opposition. The lamps have an emission at 584A and the windows are partially transparent to radiation at 584A. An electrical field is maintained between the lamps. Positive and negative ion sheaths are formed respectively on the outer surface of the two aluminum windows. Because of the electric field, the sheaths move toward opposite windows. The interaction of the ions in the sheaths and impact with the aluminum windows provide information whereby optical and electrical measurements may be made.

4 Claims, 12 Drawing Figures

COUNTER FLOWING POSITIVE ION-NEGATIVE ION NEUTRALIZATION CHROMATOGRAPH

The present invention relates generally to a chromatograph and more specifically to chromatograph using a helium resonance lamp.

The invention utilizes the mass dependence of the ion's drift velocity in an electric field and a luminescence produced by positive ion-negative ion neutralization to identify ions, measure their amounts, characterize their coefficients of reaction and identify the products of neutralization reactions.

Using deposition of helium resonance radiation energy from two resonance lamps facing each other to form counterflowing streams of positive and negative ions driven by an impressed electric field, it is possible to make optical measurements to accomplish a mass analysis of the gas sample even when several ion velocities are nearly the same.

The present device is an alternative embodiment of a high pressure ion mobility mass spectrometer which utilizes spatially resolved optical measurements to obtain an analysis of a gas sample rather than analysis based upon time measurements of a pulse excited system. Such a device is described in copending U.S. patent application Ser. No. 488,185 filed July 12, 1974 entitled "Device for Spectroscopic Measurements of Gas Composition After Addition of Helium" and filed in the name of the present inventor.

The present device is superior to known methods of analyzing a high pressure gas sample in that elaborate pumping and electronic systems are not required.

Accordingly, it is an object of this invention to provide a device for analyzing high pressure gas samples.

Another object of this invention is to provide a device for analyzing high pressure gas samples using helium resonance lamps.

These and other objects of the invention will become apparent from the following description taken together with the drawings wherein.

Broadly speaking, the present invention comprises a counter flowing positive ion-negative ion neutralization chromatograph for analyzing gas samples containing helium and a species which forms negative ions. Two helium resonance lamps are mounted in in a chamber with their windows in opposition. The lamps have an emission at 584A and the windows are partially transparent to radiation at 584A. An electrical field is maintained between the lamps. Positive and negative ion sheaths are formed respectively on the outer surface of the two aluminum windows. Because of the electric field, the sheaths move toward opposite windows. The interaction of the ions in the sheaths and impact with the aluminum windows provide information whereby optical and electrical measurements may be made.

Figure 1:
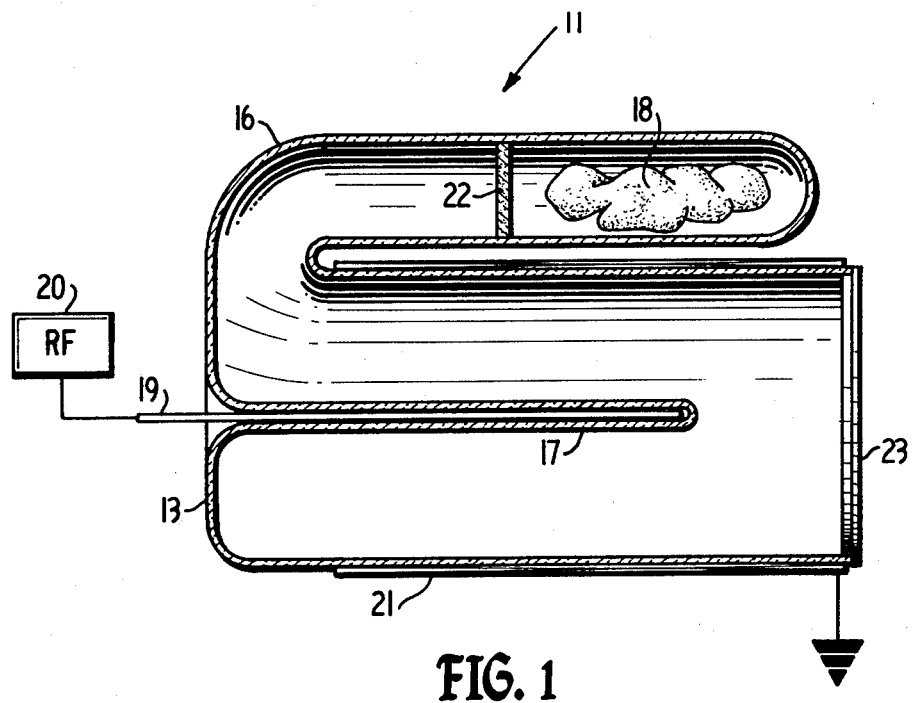
FIG. 1 is a schematic illustration of a helium resonance lamp used in the present invention.

Turning now to FIG. 1 there is shown therein a preferred embodiment of a helium resonance lamp used in the present invention. The basic structure of the lamp is described in U.S. patent application Ser. No. 426,616 now U.S. Pat. No. 3,851,214 entitled Low Power Sealed Optically Thin Resonance Lamps, filed in the name of the present inventor.

Basically, the lamp 11 comprises a hollow cylindrical body 13 having a dielectric wall, such as glass, with a reentrant coaxial hollow glass element 17 located centrally within body 13. An electrical conductor 19 is connected to a source of RF energy 20. An integral arm 16 extends from cylindrical body 13 and contains a material 18 which acts as a getter such as uranium or barium. A gas permeable filter 22 such as glass frit maintains material 18 in position. Cylindrical body 13 is filled with high purity helium and a thin window 23, preferably of aluminum, is provided so as to pass only the desired radiation.

Window 23 is partially transparent to 584A radiation. The helium gas within cylindrical body 13 is maintained at a pressure between 0.1 and 100 torr.

The cylindrical body may be covered by an electrically conductive material 21 which is electrically grounded as is schematically shown. An example of a means for accomplishing this is when cylindrical lamp body 13 is enclosed within a close fitting conductive housing which is grounded. Therefore, the lamp body is effectively sheathed by a grounded conductive element. This element completes the necessary path for electrical excitation by RF source 20.

When lamp 11 is electronically excited by the RF source 20, helium radiation is passed by the window and absorbed by He outside the lamp and, subsequently, this energy is transferred from the helium to other components of the gas mixture. This transfer may occur either directly, or through collisions of electrons, whose energy has been increased by superelastic interactions with excited helium, or as a consequence of ion neutralization (either with a free electron or with an attached electron in the form of a negative ion).

Of those materials which pass 584A, aluminum is preferred for practical reasons.

Figure 2:
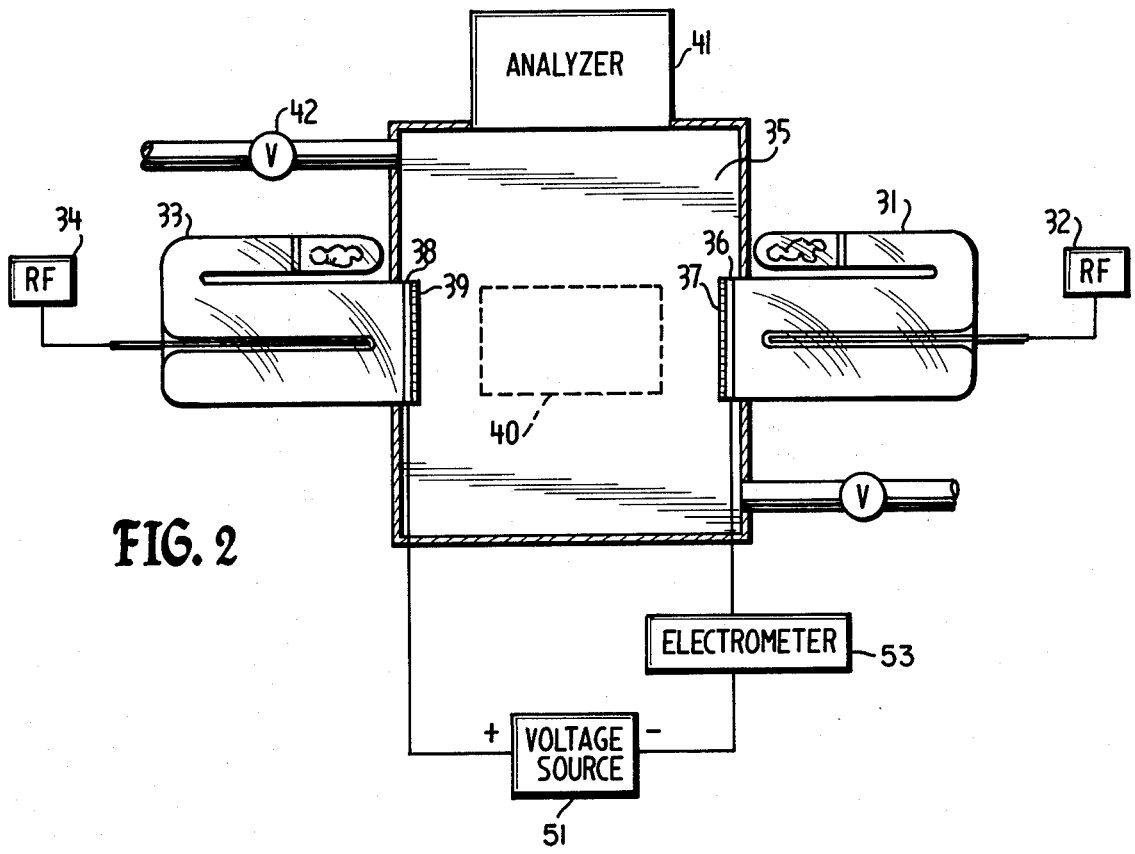
FIG. 2 is a schematic representation of the system of the present invention.
Figure 3A:
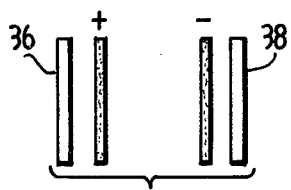
FIGS. 3a – 3e are schematic illustrations of the ion movement and reaction during operation of the device of FIG. 2.
Figure 3B:
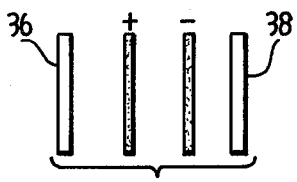
Figure 3C:
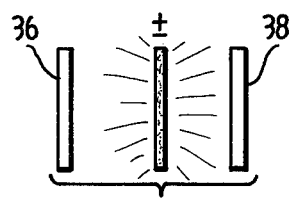
Figure 3D:
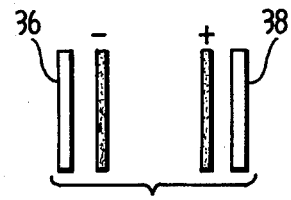
Figure 3E:
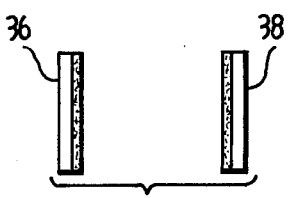

FIG. 2 is a schematic illustration of a counter-flowing positive ion-negative ion neutralization chromatograph. Two of the helium lamps 31 and 33 as described in FIG. 1 are mounted in opposed fashion within a channel 35 constructed of nonconductive material and which is supplied with the sample gas through valve 42. A measuring region 40, illustrated by dashed lines, is discussed below.

In order to measure the ion current induced in the two aluminum windows, the electrical system as shown in FIG. 2 may be used. As discussed below, an electrical field is established between the windows with one window having a positive polarity and the other having a negative polarity. The voltage source 51 is shown schematically such that window 36 is positive and window 38 is negative. An electrometer 53 is connected within the circuit to provide an output indicative of induced ion current with the aluminum windows.

FIGS. 3(a) through 3(e) show how pulsed He resonance lamps when arranged as shown in FIG. 2 can be used to constitute a counter flowing positive ion-negative ion chromatograph. The gas sample 40 contains He and another species which rapidly form stable negative ions ($Cl_2$ for example) and a gas whose positive ion it is desired to identify and measure. The two He lamps 31 and 32 are pulsed simultaneously and so create plasma sheaths 37 and 39 on the aluminum windows 36 and 38. An electric field is maintained between the two lamp windows by a power supply as shown. Because of this field, oppositely charged ion sheaths 36 and 38 move toward one another as illustrated in FIG. 3. When they meet, as in FIG. 3c, positive ion-negative ion neutralization occurs leading to excited neutral products many of which radiate their excess energy as light to a measuring device 41 such as a spectroscopic analyzer. Not all the ions are neutralized and after the ion sheaths have passed each other they continue to the appropriate conductive lamp window.

Figure 4A:
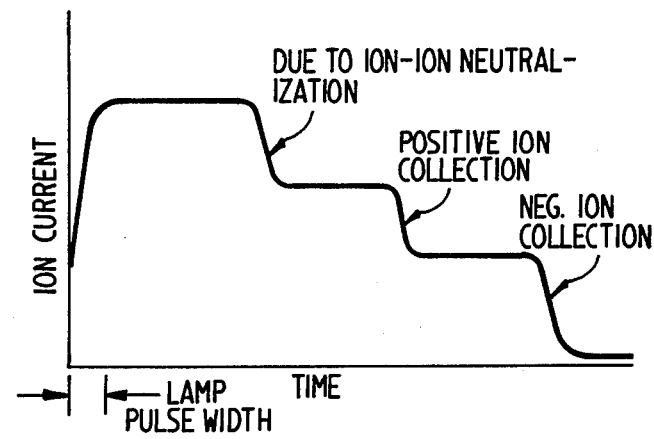
FIGS. 4a – 4c are graphic illustrations of the signal outputs of the measuring devices of FIG. 2 when the lamps are pulsed.
Figure 4B:
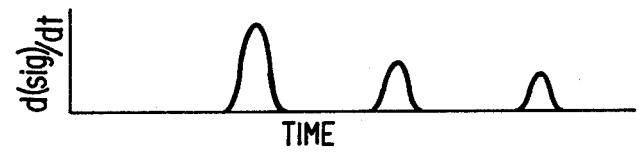

FIG. 4 indicates the electrical signal that is observed by using electrical measurement system such as electrometer 53. As shown in FIG. 4(a), there is a current step decrease when the ions meet and when each strikes the aluminum window electrode. The differentiated signal shown in FIG. 4(b) is wider for the first (ion-ion neutralization) than for the other signals because it represents the interpenetration of the two ion sheaths whose density profile is indicated by the last two peaks.

Figure 4C:
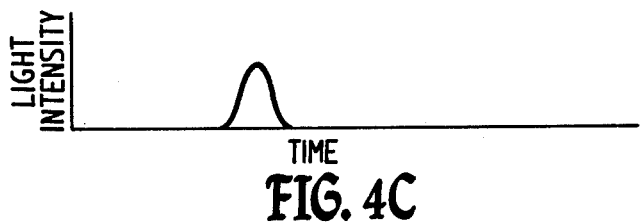

The light intensity signal, FIG. 4(c), mirrors the first differentiated current signal, and, since the velocity of one ion and the separation of the two helium lamps is know, gives the velocity, hence mobility constant, hence mass, of the other ion. Since the negative ion was formed from a deliberate additive to the gas sample it is known, and so the positive ion identity and amount can be deduced from the time displacement from the He lamp excitation pulse and amplitude of the optical signal.

The advantages to this approach are that photomultiplier detection of light using secondary electron multiplication, is more convenient, wider band, lower noise, and less expensive than current measurements. Furthermore, spectral resolution of the emission could lead to identification and measurement of overlapping ion sheaths that contain ions of very similar mobility (i.e. which give overlapping light delays).

If a spectrograph slit (not shown) is aligned with the ion motion, and the region between the aluminum windows is focused on the spectrograph slit, the spatial location of the ion-ion recombination readiation along the slit can be used to obtain the ion mobility and mass while simultaneously wavelength analyzing the radiation.

Figure 5A:
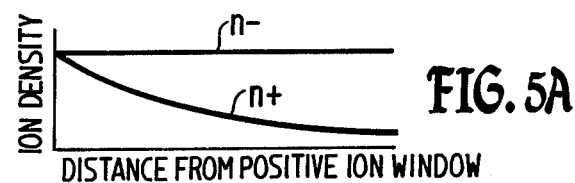
FIGS. 5a and 5b are graphic illustrations of the signal outputs of the measuring devices when the lamps are operated continuously.
Figure 5B:
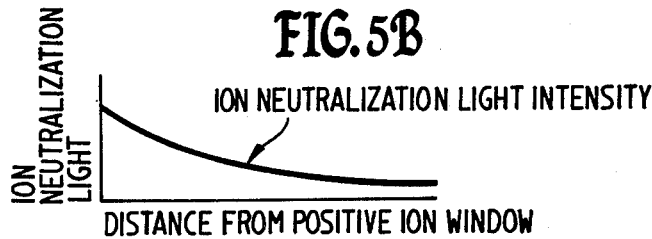

If both He lamps are not pulsed but are operated continuously, the simple situation depicted in FIG. 5 occurs only if either the negative ion concentration greatly exceeds the positive ion concentration or vice versa. Since the negative ions are formed from species purposely added to the sample gas, it is possible to make their concentration much larger than that of the positive ions.

The positive ions then decrease exponentially in concentration as a function of distance from the positive lamp aluminum window. The distance variation can be observed by measuring the distance variation of the emission amplitude of the ion neutralization process. This process causes the decrease in the positive ion density, $n_+$ as a function of the distance from the positive aluminum window. The rate of decay of $n_+$ with distance from the positive lamp window, $\alpha_i$, depends upon $n_-$, the negative ion concentration, $v_+$ the positive ion velocity and the ion neutralization reaction rate coefficient $k_i$ and is given by $\alpha_i = k_i n_-/v_i$. A measure of $\alpha_i$, $n_-$, $v_i$ given $k_i$. The velocity $v_i$ is derivable as shown in FIG. 4, $n_-$ is obtained by measuring the negative ion current $i_- = V_- n_-$, then, knowing $V_-$, obtaining $n_- = i_-/v_-$. In any case, empirical calibration permits each measured $\alpha_i$ to be associated with a unique ion and the intensity $I_i$, of the recombination radiation at a fixed $x, x_0$, can be calibrated to give the concentration of the parent neutral species producing the positive ion.

The above description and drawings are illustrative only since equivalents could be substituted without departing from the invention. Accordingly, the invention is to be limited only by the scope of the following claims.

I claim:

1. A counter flowing positive ion-negative ion neutralization chromatograph for analyzing gas samples containing helium and a species which forms stable negative ions comprising
    a channel constructed of electrically non conducting material for receiving said gas sample;
    a first helium resonance lamp having an emission at 584A;
    a window in said first lamp partially transparent to radiation at 584A, said lamp being mounted with said window extending within said channel;
    a second helium resonance lamp having an emission at 584A and opposite the first helium lamp;
    a window in said second lamp partially transparent to radiation at 584A, said second lamp being mounted with said window extending within said channel, said windows being spaced in opposing relationship;
    means for simultaneously exciting said lamps;
    means for maintaining potential difference between the windows; and
    means in said channel for measuring the intensity, wavelength, and position of emitted radiation between said windows.

2. The chromatograph of claim 1 wherein said window is aluminum.

3. The chromatograph of claim 1 wherein said means for maintaining said potential difference is a pulsed voltage source.

4. The chromatograph of claim 1 wherein said means for maintaining said potential difference is a continuous voltage source.

* * * * *